US006998131B2

(12) United States Patent
Soll et al.

(10) Patent No.: US 6,998,131 B2
(45) Date of Patent: Feb. 14, 2006

(54) SPOT-ON FORMULATIONS FOR COMBATING PARASITES

(75) Inventors: Mark D. Soll, Alpharetta, GA (US); Albert Boeckh, Cumming, GA (US)

(73) Assignee: Merial Limited, Duluth, GA (US)

( * ) Notice: Subject to any disclaimer, the term of this patent is extended or adjusted under 35 U.S.C. 154(b) by 240 days.

(21) Appl. No.: 10/279,356

(22) Filed: Oct. 24, 2002

(65) Prior Publication Data

US 2003/0166688 A1 Sep. 4, 2003

Related U.S. Application Data

(60) Continuation-in-part of application No. 10/155,397, filed on May 24, 2002, which is a division of application No. 09/376,736, filed on Aug. 17, 1999, now Pat. No. 6,426,333, which is a continuation-in-part of application No. 09/271,470, filed on Mar. 17, 1999, now Pat. No. 6,482,425, which is a continuation-in-part of application No. PCT/FR97/01548, filed on Sep. 15, 1997.

(30) Foreign Application Priority Data

Sep. 19, 1996 (FR) .................................. 96 11446

(51) Int. Cl.
*A01N 25/32* (2006.01)

(52) U.S. Cl. ................... 424/406; 424/405; 424/78.07; 514/30; 514/407

(58) Field of Classification Search ................ 424/405, 424/406, 78.07; 514/27, 28, 30, 407, 919
See application file for complete search history.

(56) References Cited

U.S. PATENT DOCUMENTS 4,260,775 A 4/1981 Plath et al.
(Continued)

FOREIGN PATENT DOCUMENTS

EP 0295117 A1 12/1988
(Continued)

OTHER PUBLICATIONS

Database CABA STN-International STN-accession No. 95:202002, J.M. Postal, "Efficacy of 0.25 Fipronil Based Formulation Spray In The Treatment and Prevention of Flea Infestations of Dogs and Cats", XP002028860 vori abrege & Professione Veterinaria, No. 1, 1995, pp. 17-18.
(Continued)

*Primary Examiner*—Neil S. Levy
(74) *Attorney, Agent, or Firm*—Frommer Lawrence & Haug; Thomas J. Kowalski; Judy Jarecki-Black

(57) ABSTRACT

In particular this invention provides for spot-on compositions for the treatment or prophylaxis of parasite infestations in mammals or birds which comprise:
(1) a composition comprising
(A) an effective amount of a 1-phenylpyrazole derivative; and
(B) an effective amount of emamectin;
(2) an acceptable liquid carrier vehicle; and
(3) optionally, a crystallization inhibitor.

The invention also provides for a method of treating parasitic infestations or for the prophylaxis of parasite infestations in mammals or birds which comprises topically applying to said mammal treating parasitic infestations or for the prophylaxis of parasite infestations in mammals or birds which comprises topically applying to said mammal or bird an effective amount of a composition according to the present invention.

51 Claims, 2 Drawing Sheets

Efficacy against Ticks

U.S. PATENT DOCUMENTS

| Patent No. | Date | Inventor |
|---|---|---|
| 4,298,749 A | 11/1981 | Plath et al. |
| 4,451,479 A | 5/1984 | Dusza et al. |
| 4,496,390 A | 1/1985 | Hatton et al. |
| 4,803,215 A | 2/1989 | Jensen-Korte et al. |
| 4,845,089 A | 7/1989 | Lindig et al. |
| 4,963,575 A | 10/1990 | Buntain et al. |
| 5,055,482 A | 10/1991 | Hatton et al. |
| 5,077,278 A | 12/1991 | Hafner et al. |
| 5,104,994 A | 4/1992 | Roberts et al. |
| 5,177,100 A | 1/1993 | Roberts et al. |
| 5,232,940 A | 8/1993 | Hatton et al. |
| 5,236,938 A | 8/1993 | Huang et al. |
| 5,240,915 A | 8/1993 | Rosegay |
| 5,360,910 A | 11/1994 | Huang et al. ............... 546/279 |
| 5,387,509 A | 2/1995 | Hawrylik et al. |
| 5,516,787 A | 5/1996 | Takada |
| 5,547,974 A | 8/1996 | Hatton et al. |
| 5,556,868 A | 9/1996 | Banks |
| 5,556,873 A | 9/1996 | Huang et al. |
| 5,567,429 A | 10/1996 | Senbo |
| 5,602,107 A | 2/1997 | Choi |
| 5,608,077 A | 3/1997 | Hatton et al. |
| 5,614,182 A | 3/1997 | Davidson et al. |
| 5,677,332 A | 10/1997 | Banks |
| 5,700,460 A | 12/1997 | Davidson et al. |
| 5,714,191 A | 2/1998 | Hutton et al. |
| 5,723,488 A | 3/1998 | Walshe |
| 5,733,887 A | 3/1998 | Walshe |
| 5,739,083 A | 4/1998 | Endo et al. |
| 5,747,519 A | 5/1998 | Kodama et al. |
| 5,817,688 A | 10/1998 | Huang et al. |
| 5,883,080 A | 3/1999 | Dutton et al. |
| 5,916,618 A | 6/1999 | Hatton et al. |
| 5,916,909 A | 6/1999 | Kodama et al. |
| 5,972,330 A | 10/1999 | Sugiura et al. |
| 5,977,156 A | 11/1999 | Duvert et al. |
| 5,981,500 A | 11/1999 | Bishop et al. |
| 6,054,140 A | 4/2000 | Lamberti |

FOREIGN PATENT DOCUMENTS

| | | |
|---|---|---|
| EP | 0500209 A1 | 8/1992 |
| EP | 0679650 A1 | 11/1995 |
| FR | 2 713 889 A | 6/1995 |
| WO | WO 95/20875 | 8/1995 |
| WO | 96 16543 A | 6/1996 |
| WO | 96/16544 * | 6/1996 |
| WO | 97/140692 * | 11/1997 |
| WO | WO 00/30449 | 6/2000 |

OTHER PUBLICATIONS

Research Disclosure, "Extended Efficacy Spectrum of Azole Pesticides" No. 380, Dec. 1, 1995, Havant GB, p. 802, XP00549823 voir le document en entier.

Data WPI, Section Ch, Week 9240, Derwent Publications Ltd., London, GB, Class C02, AN 92-327692 (Aug. 24, 1992) XP 002028892 & JP 04 235 104 A (Mitsubishi Kasei Corp.), Aug. 24, 1992. voir abrege.

R. Atwell et al., The Effects of Fipronil on Ix0des Holocyclus on Dogs in Northern NSW, Australian Veterinary Practitioner, vol. 26, No. 3, Sep. 3, 1996, p. 155 XP 000647073, voir le document en entire.

P.R. Cooper, et al., "Use of Fipronil To eliminate Recurrent Infestation By *Trichodectes Canis* In a Pack of Bloodhounds", The Veterinary Record, vol. 193(Sep. 1996) p. 95.

Database CABA, STN-International, STN-accession No. 95:202003, C. Genchi, et al., "Efficacy of Fipronil In a Spray Formulation", (Frontline RM) in Treating Flea and Tick Infestation On Dogs XP 002028859, voir abrege & Professione Veterinaria No. 1, (suppl.), 1995, pp. 19-22.

\* cited by examiner

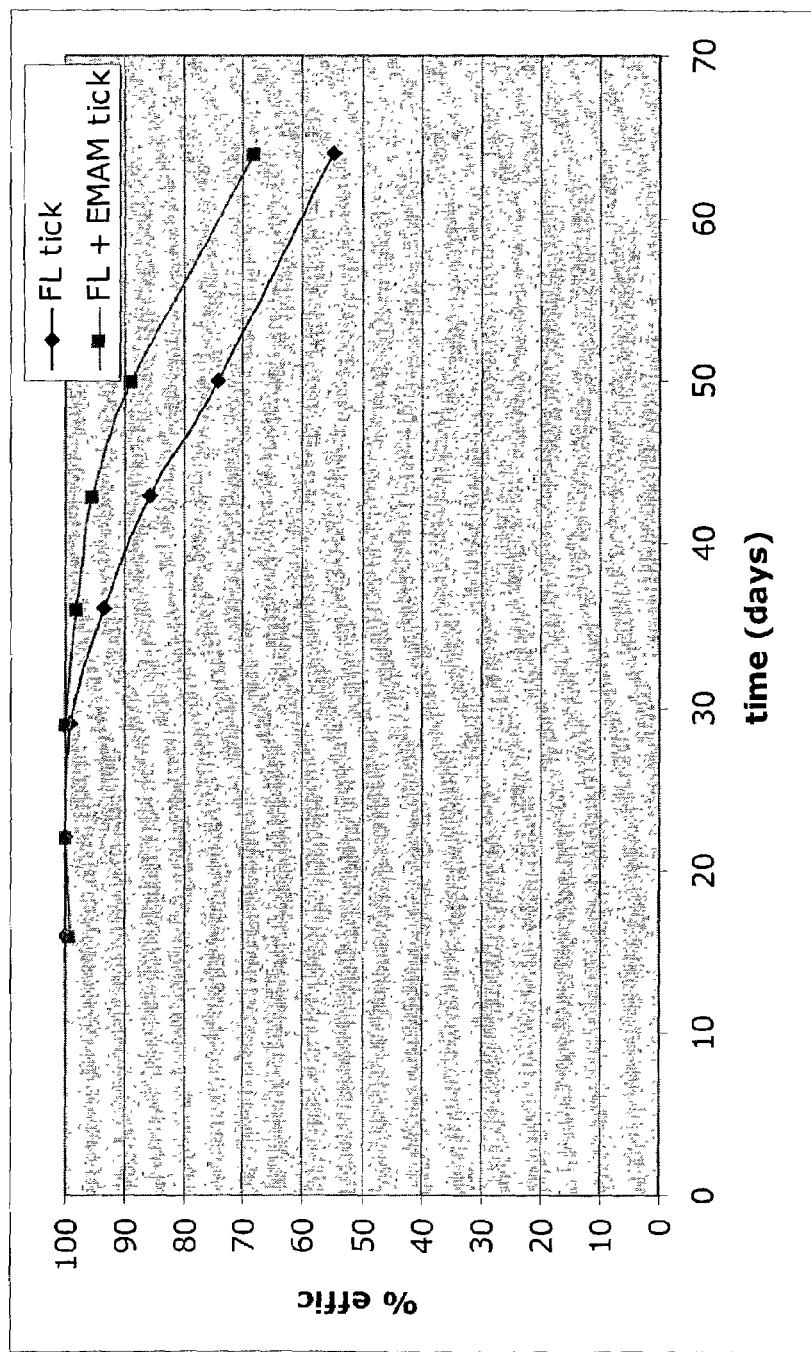
Fig. 1 Efficacy against Ticks

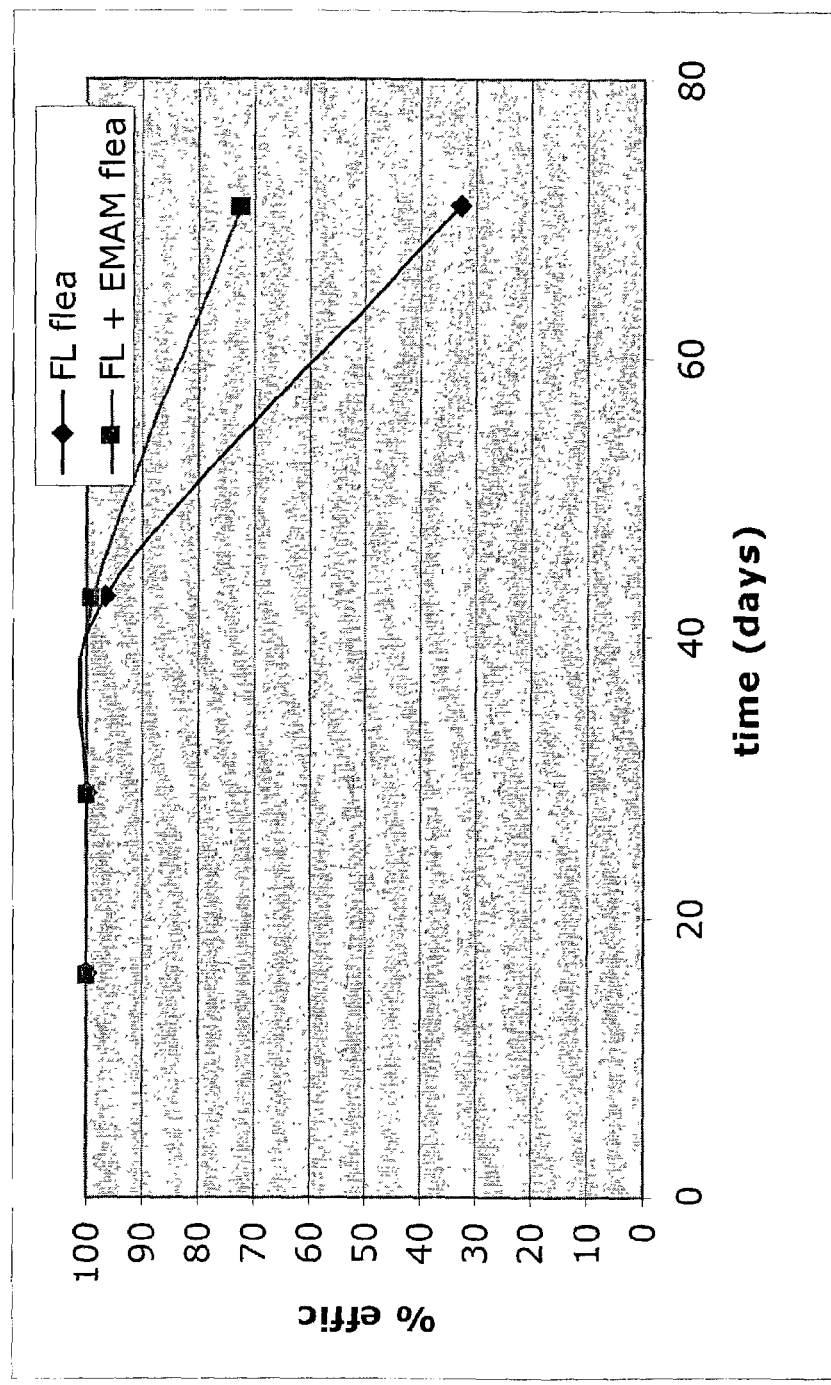
Fig. 2  Efficacy against Fleas

SPOT-ON FORMULATIONS FOR COMBATING PARASITES

RELATED APPLICATIONS

This application is a continuation-in-part of application U.S. Ser. No. 10/155,397, filed May 24, 2002, now pending, which in turn is a divisional of application Ser. No. 09/376,736, filed Aug. 17, 1999, now U.S. Pat. No. 6,426,333 issued on Jul. 30, 2002, which in turn is a continuation in-part of application U.S. Ser. No. 09/271,470, filed Mar. 17, 1999, now U.S. Pat. No. 6,482,425, which in turn is a continuation-in-part of copending International Application PCT/FR97/01548 having an international filing date of 15 Sep. 1997, and designating the U.S. and claiming priority from French Application No. 96/11446, filed 19 Sep. 1996. Reference is also made to: U.S. application Ser. No. 08/719,942, filed Sep. 25, 1996, Ser. No. 08/692,430, filed Aug. 5, 1996, Ser. No. 08/863,182, filed May 27, 1997, Ser. No. 08/692,113, filed Aug. 5, 1996, Ser. No. 08/863,392, filed May 27, 1997, and Ser. No. 08/891,047, filed Jul. 10, 1997; French Application No. 97 03709, filed Mar. 26, 1997; and PCT/FR98/00601. All of the above-mentioned applications, as well as all documents cited herein and documents referenced or cited in documents cited herein, are hereby incorporated herein by reference.

FIELD OF THE INVENTION

This invention relates to spot-on formulations for combating parasites in birds and mammals. In particular, this invention provides for spot-on formulations comprising a composition comprising a 1-N-phenylpyrazole derivative and/or a macrolide anthelmintic or antiparasitic agent, and a pharmaceutically or veterinary acceptable liquid carrier vehicle. This invention also provides for to an improved method for eradicating, controlling, and preventing parasite infestation in birds and mammals.

BACKGROUND OF THE INVENTION

Animals such as mammals and birds are often susceptible to parasite infestations. These parasites may be ectoparasites, such as insects, and endoparasites such as filariae and worms.

Domesticated animal, such as cats and dogs, are often infested with one or more of the following ectoparasites:
cat and dog fleas (*Ctenocephalides felis, Ctenocephalides* sp. and the like),
ticks (*Rhipicephalus* sp., *Ixodes* sp., *Dermacentor* sp., *Amblyoma* sp. and the like), and
mites (*Demodex* sp., *Sarcoptes* sp., *Otodectes* sp. and the like),
lice (*Trichodectes* sp., *Cheyletiella* sp., *Lignonathus* sp., and the like),
mosquitoes (*Aedes* sp., *Culux* sp., *Anopheles* sp., and the like) and
flies (*Hematobia* sp., *Musca* sp., *Stomoxys* sp., *Dematobia* sp., *Coclyomia* sp., and the like).

Fleas are a particular problem because not only do they adversely affect the health of the animal or human, but they also cause a great deal of psychological stress. Moreover, fleas are also vectors of pathogenic agents in animals, such as dog tapeworm (*Dipylidium caninum*), and humans.

Similarly, ticks are also harmful to the physical and psychological health of the animal or human. However, the most serious problem associated with ticks is that they are the vector of pathogenic agents, agents which cause diseases in both humans and animal. Major diseases which are caused by ticks include borrelioses (Lyme disease caused by *Borrelia burgdorferi*), babesioses (or piroplasmoses caused by *Babesia* sp.) and rickettsioses (also known as Rocky Mountain spotted fever). Ticks also release toxins which cause inflammation or paralysis in the host. Occasionally, these toxins are fatal to the host.

Moreover, mites and lice are particularly difficult to combat since there are very few active substances which act on these parasites and they require frequent treatment.

Likewise, farm animals are also susceptible to parasite infestations. For example, cattle are affected by a large number of parasites. A parasite which is very prevalent among farm animals is a tick genus *Boophilus*, especially those of the species microplus (cattle tick), decoloratus and anulatus. Ticks, such as *Boophilus microplus*, are particularly difficult to control because they live in the pasture where the farm animals graze. Other important parasites of cattle and sheep are listed as follows in order of decreasing importance:

myiases such as *Dermatobia hominis* (known as Berne in Brazil) and *Cochlyomia hominivorax* (greenbottle); sheep myiases such as *Lucilia sericata, Lucilia cuprina* (known as blowfly strike in Australia, New Zealand and South Africa). These are flies whose larva constitutes the animal parasite;

flies proper, namely those whose adult constitutes the parasite, such as *Haematobia irritans* (horn fly);

lice such as *Linognathus vitulorum*, etc.; and mites such as *Sarcoptes scabici* and *Psoroptes ovis*.

The above list is not exhaustive and other ectoparasites are well known in the art to be harmful to animals and humans. These include, for example migrating dipterous larvae.

Animals and humans also suffer from endoparasitical infections including, for example, helminthiasis which is most frequently caused by a group of parasitic worms described as nematodes or roundworms. These parasites cause severe economic losses in pigs, sheep, horses, and cattle as well as affecting domestic animals and poultry. Other parasites which occur in the gastrointestinal tract of animals and humans include *Ancylostoma, Anecator, Ascaris, Strongyloides, Trichinella, Capillaria, Toxocara, Toxascaris, Trichiris, Enterobius* and parasites which are found in the blood or other tissues and organs such as filarial worms and the extra intestinal stages of *Strogyloides, Toxocara* and *Trichinella*.

Many insecticides exist in the art for treating parasites. These insecticides vary in their effectiveness to a particular parasite as well as their cost. However the results of these insecticides is not always satisfactory because of, for example, the development of resistance by the parasite to the therapeutic agent, as is the case, for example, with carbamates, organophosphorus compounds and pyrethroids. Moreover, there is at the present time no truly effective method for controlling both ticks and helminths and less still an effective way of controlling the set of parasites indicated above. Thus, there is a need in the art for more effective antiparasitic formulation treatment and protection of animal, e.g. mammals, fish and birds for a wide range of parasites. Moreover, there is a need in the art for antiparasitic formulation which is easy to use on any type of domestic animal, irrespective of its size and the nature of its coat and which do not need to be sprinkled over the entire body of the mammal, fish or bird.

A new family of insecticides based on 1-N-phenylpyrazoles is described in Patents EP-A-295,217 and EP-A-352,944. The compounds of the families defined in these patents are extremely active and one of these compounds, 1-[2,6-Cl$_2$-4-CF$_3$ phenyl]-3-CN-4-[ SO—CF$_3$]-5-NH$_2$ pyrazole, or fipronil, is particularly effective, not only against crop parasites but also against ectoparasites of mammals and birds. Fipronil is particularly, but not exclusively, effective against fleas and ticks.

Endectocidal compounds, which exhibit a degree of activity against a wide range endoparasites, are known in the art. These compounds possess a macrocyclic lactone ring and are known in the art to be particularly effective against ectoparasites, including lice, blowflies, flies, mosquitoes, mites, migrating dipterous larvae, and ticks, as well as endoparasites, such as nematodes and roundworms. Compounds of this group include avermectins, milbemycins, and derivatives of these compounds, for example, ivermectin or emamectin. Such substances are described, for example, in U.S. Pat. Nos. 3,950,360; 4,199,569; 4,879,749; and 5,268,710.

While it is known in the art that it is sometimes possible to combine various parasiticides in order to broaden the antiparasitical spectrum, it is not possible to predict, a priori, which combinations will work for a particular animal or disease state. For this reason, the results of various combinations is not always successful and there is a need in the art for more effective formulations which may be easily administered to the animal. The effectiveness of formulations comprising 1-N-phenylpyrazole derivatives and macrolide lactone anthelmintic or parasitic agents, such as avermectins, ivermectins and milbemycin, against an endoparasite or an ectoparasite in a specific host is especially difficult to predict because of the numerous and complex host-parasite interactions.

Patent application AU-A-16 427/95 very broadly mentions the combination of a substituted 1-N-pyrazole derivatives with an avermectin, ivermectin or moxidectin in a discussion involving among a very large number of insecticides or parasiticides of various types, including fipronil. However, this patent application does not provide specific guidance to the skilled artisan on how to formulate a 1-N-pyrazole derivative with an avermectin or milbemycin type compound, let alone how to formulate a spot-on composition comprising these compounds. Moreover, the application does not indicate which specific parasites are susceptible to what specific combination.

Various methods of formulating antiparasitical formulations are known in the art. These include oral formulations, baits, dietary supplements, powders, shampoos, etc. Formulations for localized topical applications of antiparasitical formulations are also known in the art. For example, pour-on solutions comprising 1-N-phenylpyrazoles, such as fipronil, are known in the art and are described in copending application Ser. No. 08/933,016, herein incorporated by reference. Other methods of formulating antiparasitic agents include spot-on formulations.

Spot-on formulations are well known techniques for topically delivering an antiparasitic agent to a limited area of the host. For example, U.S. Pat. No. 5,045,536 describes such formulations for ectoparasites. Moreover, it is generally known in the art to formulate avermectin and milbemycin derivatives as spot-on formulations. See, e.g. U.S. Pat. No. 5,045,536; EP 677,054; U.S. Pat. No. 5,733,877; U.S. Pat. No. 5,677,332; U.S. Pat. No. 5,556,868; and U.S. Pat. No. 5,723,488. However, as discussed in U.S. Pat. No. 5,045,536, a large number of solvent systems described in the art provide formulations for localized topical application which cause irritancy or toxicity to the host. Hence, there is a need in the art both for more effect and less irritant or toxic formulations. Thus, there is a need in the art for a spot-on formulation which is effect against a wide range of endoparasites and ectoparasites in birds and mammals.

BRIEF DESCRIPTION OF THE DRAWINGS

FIG. 1 compares the efficacy against ticks in dogs for the topical application of a topical composition comprising fipronil against the efficacy of a topical application comprising fipronil and emamectin.

FIG. 2 compares the efficacy against fleas in dogs for the topical application of a topical composition comprising fipronil against the efficacy of a topical application comprising fipronil and emamectin.

SUMMARY OF THE INVENTION

The invention provides for spot-on formulations for the treatment or prophylaxis of parasites of mammals, fish and birds, and in particular, cats, dogs, horses, chickens, sheep and cattle with the aim of ridding these hosts of all the parasites commonly encountered by birds and mammals. The invention also provides for effective and lasting destruction of ectoparasites, such as fleas, ticks, mites, e.g. itch mites, mosquitoes, flies and lice, and of endoparasites, nematodes, such as filariae, and roundworms of the digestive tract of animals and humans.

In particular this invention provides for spot-on formulations for the treatment or prophylaxis of parasite infestations in mammals or birds which comprise:

(1) a composition comprising
  (A) an effective amount of a 1-N-phenylpyrazole derivative; and
  (B) an effective amount of a macrocyclic lactone antihelmintic or antiparasitic agent such as emamectin;
(2) a pharmaceutically or veterinary liquid carrier vehicle; and
(3) optionally, a crystallization inhibitor.

The invention also provides for an easy method of treating parasitic infestations or for the prophylaxis of parasite infestations in mammals or birds which comprises topically applying to said mammal or bird an effective amount of a formulation according to the present invention.

This invention also provides for spot-on formulations comprising a combination comprising a compound of formula (I) and a macrocyclic lactone which exhibit synergistic activity against parasites when compared to formulations which contain only one class of therapeutic agent.

This invention further provides for formulations which, when applied locally, will diffuse over the entire body of the host and then dry, without crystallizing, and which do not affect the appearance of the coat after drying by, for example, leaving crystals or making the coat sticky. This has the further advantage in animals which groom themselves of not being orally ingested, where the therapeutic agent might not be well tolerated orally or might interact with other therapeutic agents.

The very high effectiveness of the method and of the formulations according to the invention provides not only for a high instantaneous effectiveness but also for an effectiveness of very long duration after the treatment of the animal.

These and other embodiments are disclosed or are obvious from and encompassed by, the following Detailed Description.

DETAILED DESCRIPTION

This invention provides for a spot-on formulation for the treatment and prophylaxis of parasite infestation in mammals or birds which comprises
(1) a composition comprising
   (A) an effective amount of at least one compound of the formula

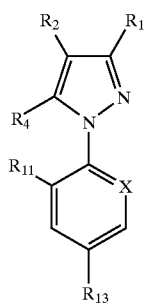

(I)

in which:
   $R_1$ is a halogen atom, CN or methyl;
   $R_2$ is $S(O)_n R_3$ or 4,5-dicyanoimidazol-2-yl or haloalkyl;
   $R_3$ is alkyl or haloalkyl;
   $R_4$ represents a hydrogen or halogen atom or an $NR_5R_6$, $S(O)_m R_7$, $C(O)R_7$ or $C(O)OR_7$, alkyl, haloalkyl or $OR_8$ radical or an —N=C($R_9$)($R_{10}$) radical;
   $R_5$ and $R_6$ independently represent a hydrogen atom or an alkyl, haloalkyl, C(O)alkyl, $S(O)_r CF_3$ or alkoxycarbonyl radical or $R_5$ and $R_6$ can together form a divalent alkylene radical which is optionally interrupted by one or two divalent heteroatoms;
   $R_7$ represents an alkyl or haloalkyl radical;
   $R_8$ represents an alkyl or haloalkyl radical or a hydrogen atom;
   $R_9$ represents an alkyl radical or a hydrogen atom;
   $R_{10}$ represents an optionally substituted aryl or an optionally substituted heteroaryl group;
   $R_{11}$ and $R_{12}$ represent, independently of one another, hydrogen, halogen CN or $NO_2$;
   $R_{13}$ represents a halogen atom or a haloalkyl, haloalkoxy, $S(O)_q CF_3$ or $SF_5$ group;
   m, n, q and r represent, independently of one another, an integer equal to 0, 1 or 2;
   X represents a trivalent nitrogen atom or a C—$R_{12}$ radical, the three other valencies of the carbon atom forming part of the aromatic ring;
   with the proviso that, when $R_1$ is methyl, then either $R_3$ is haloalkyl, $R_4$ is $NH_2$, $R_{11}$ is Cl, $R_{13}$ is $CF_3$ and X is N or else $R_2$ is 4,5-dicyanoimidazol-2-yl, $R_4$ is Cl, $R_{11}$ is Cl, $R_{13}$ is $CF_3$ and X is C—Cl; and/or
   (B) a pharmaceutical or veterinary effective amount of a macrocyclic lactone antihelmintic or antiparasitic agent such as emamectin;
(2) a pharmaceutically or veterinary acceptable liquid carrier vehicle; and
(3) optionally, a crystallization inhibitor More preferably, this invention provides for a spot-on formulation which comprises:
(1) a composition comprising
   (A) an effective amount of a compound of formula (I) wherein
   $R_1$ is a halogen atom, CN or methyl;
   $R_2$ is $S(O)_n R_3$ or 4,5-dicyanoimidazol-2-yl or haloalkyl;
   $R_3$ is $C_1$–$C_6$-alkyl or $C_1$–$C_6$-haloalkyl;
   $R_4$ represents a hydrogen or halogen atom; or a radical $NR_5R_6$, $S(O)_m R_7$, $C(O)R_7$ or $C(O)OR_7$, alkyl, haloalkyl or $OR_8$ or a radical —N=C($R_9$)($R_{10}$);
   $R_5$ and $R_6$ independently represent a hydrogen atom or a $C_1$–$C_6$-alkyl, $C_1$–$C_6$-haloalkyl, $C(O)C_1$–$C_6$-alkyl, $S(O)_r CF_3$, $C_1$–$C_6$-acyl or $C_1$–$C_6$-alkoxycarbonyl radical; or $R_5$ and $R_6$ may together form a divalent alkylene radical which may be interrupted by one or two divalent hetero atoms selected from the group consisting of oxygen or sulphur;
   $R_7$ represents a $C_1$–$C_6$-alkyl or $C_1$–$C_6$-haloalkyl radical;
   $R_8$ represents a $C_1$–$C_6$-alkyl or $C_1$–$C_6$-haloalkyl radical or a hydrogen atom;
   $R_9$ represents a $C_1$–$C_6$-alkyl radical or a hydrogen atom;
   $R_{10}$ represents an optionally substituted phenyl or optionally substituted heteroaryl group wherein the substituents are selected from the group consisting of halogen, OH, —O—$C_1$–$C_6$-alkyl, —S—$C_1$–$C_6$-alkyl, cyano or $C_1$–$C_6$-alkyl;
   $R_{11}$ and $R_{12}$, independently of one another represent hydrogen, halogen, CN or $NO_2$;
   $R_{13}$ represents a halogen, $C_1$–$C_6$-haloalkyl, $C_1$–$C_6$-haloalkoxy, $S(O)_q Cl_3$ or $SF_5$ group, and/or
   (B) an effective amount of a macrocyclic lactone selected from the group consisting of avermectins, ivermectin, abamectin, doramectin, emamectin, moxidectin, selamectin, milbemycins and their derivatives with emamectin being especially preferred;
(2) the liquid carrier vehicle comprises a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, in particular N-methylpyrrolidone, diethylene glycol monoethyl ether, ethylene glycol, diethyl phthalate fatty acid esters, such as the diethyl ester or diisobutyl adipate, and a mixture of at least two of these solvents and the cosolvent is selected from the group consisting of absolute ethanol, isopropanol or methanol.
(3) a crystallization inhibitor selected from the group consisting of an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, and acrylic derivatives, or a mixture of these crystallization inhibitors.

Especially preferred are spot-on formulations described above wherein both compounds of formula I and a macrocyclic lactone antihelmintic or antiparasitic agent such as emamectin are present. Especially more preferred are more composition wherein the ring formed by the divalent alkylene radical representing $R_5$ and $R_6$ and the nitrogen atom to which $R_5$ and $R_6$ are attached has 5, 6 or 7 members or wherein $R_1$ is CN, $R_3$ is $C_1$–$C_6$-haloalkyl, $R_4$ is $NH_2$, $R_{11}$ and $R_{12}$ are, independently of one another, hydrogen or halogen and $R_{13}$ is $C_1$–$C_6$-haloalkyl.

Most especially preferred are spot-on compositions, wherein the composition comprises:

(A) 1-[2,6-$Cl_2$-4-$CF_3$ phenyl]-3-CN-4-[SO—$CF_3$]-5-$NH_2$ pyrazole; and (B) ivermectin and milbemectin; or where the composition comprises (A) 1-[2,6-$Cl_2$-4-$CF_3$ phenyl]-3-CN-4-[SO—$CF_3$]-5-$NH_2$ pyrazole; and (B) selamectin or emamectin.

The phenylpyrazoles ("compound A") as a class are known in the art and are described, for example, in copending applications U.S. Ser. Nos. 07/719,942; 08/933,016; 09/174,598; 08/863,182; and 08/863,692, as well as in U.S. Pat. No. 5,576,429; U.S. Pat. No. 5,122,530, and EP 295 177, the disclosures of which, as well as the references cited herein, are incorporated by reference. This class of insecticides is known to possess excellent activity against insects. such as ticks and fleas.

The macrocyclic lactone antihelmintic or parasitic agents ("compound B") are well known to a person skilled in the art and are easily obtained either commercially or through techniques know in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216–4221. For doramectin, "Veterinary Parasitology", vol. 49, No. 1, July 1993, 5–15 may in particular be consulted. For milbemycins, reference may be made, inter alia, to Davies H. G. et al., 1986, "Avermectins and Milbemycins", Nat. Prod. Rep., 3, 87–121, Mrozik H. et al., 1983, Synthesis of Milbemycins from Avermectins, Tetrahedron Lett., 24, 5333–5336, U.S. Pat. No. 4,134,973 and EP 677,054.

Compounds (B) are either natural products or are semisynthetic derivatives thereof. The structure of at least certain compounds (B) are closely related, e.g., by sharing a complex 16-membered macrocyclic lactone ring. The natural product avermectins are disclosed in U.S. Pat. No. 4,310,519 to Albers-Schönberg, et al., and the 22,23-dihydro avermectin compounds are disclosed in Chabala, et al., U.S. Pat. No. 4,199,569. Mention is also made of Kitano, U.S. Pat. No. 4,468,390, Beuvry et al., U.S. Pat. No. 5,824,653, European Patent Application 0 007 812 A1, published Jun. 2, 1980, U.K. Patent Specification 1 390 336, published Apr. 9, 1975, European Patent Application 0 002 916 A2, and Ancare New Zealand Patent No. 237 086, inter alia. Naturally occurring milbemycins are described in Aoki et al., U.S. Pat. No. 3,950,360 as well as in the various references cited in "The Merck Index" 12$^{th}$ ed., S. Budavari, Ed., Merck & Co., Inc. Whitehouse Station, N.J. (1996). Semisynthetic derivatives of these classes of compounds are well known in the art and are described, for example, in U.S. Pat. No. 5,077,308, U.S. Pat. No. 4,859,657, U.S. Pat. No. 4,963,582, U.S. Pat. No. 4,855,317, U.S. Pat. No. 4,871,719, U.S. Pat. No. 4,874,749, U.S. Pat. No. 4,427,663, U.S. Pat. No. 4,310,519, U.S. Pat. No. 4,199,569, U.S. Pat. No. 5,055,596, U.S. Pat. No. 4,973,711, U.S. Pat. No. 4,978,677, U.S. Pat. No. 4,920,148 and EP 667,054.

Particularly preferred macrocyclic lactones are avermectin derivatives which are monosaccharides and have a 5-oxime substituent. Particularly preferred derivatives are:

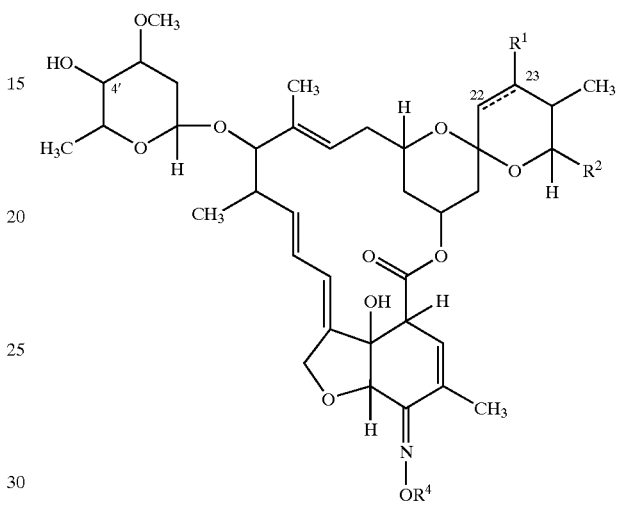

wherein the broken line at the 22-23 position represents an optional bond, $R^1$, when present, is a hydrogen or a hydroxyl group, $R^2$ is, for example, alkyl or cycloalkyl group and $R^3$ is, for example, hydrogen or alkyl. An especially preferred compound of this general structure is selamectin which has the following structure:

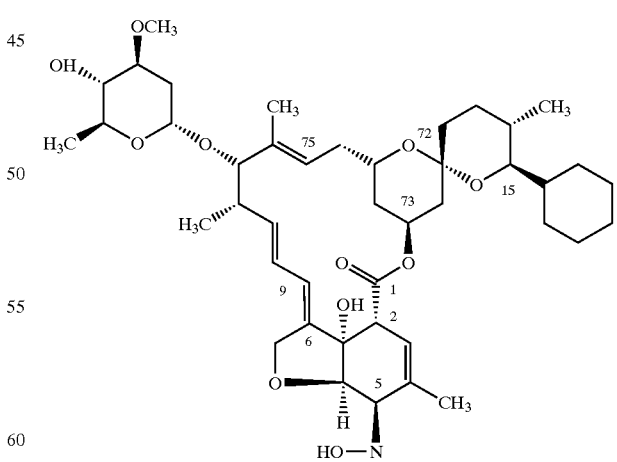

These compounds are known in the art and are described for example in EP 667,054. An other especially preferred compound is emamectin, which has the following structure:

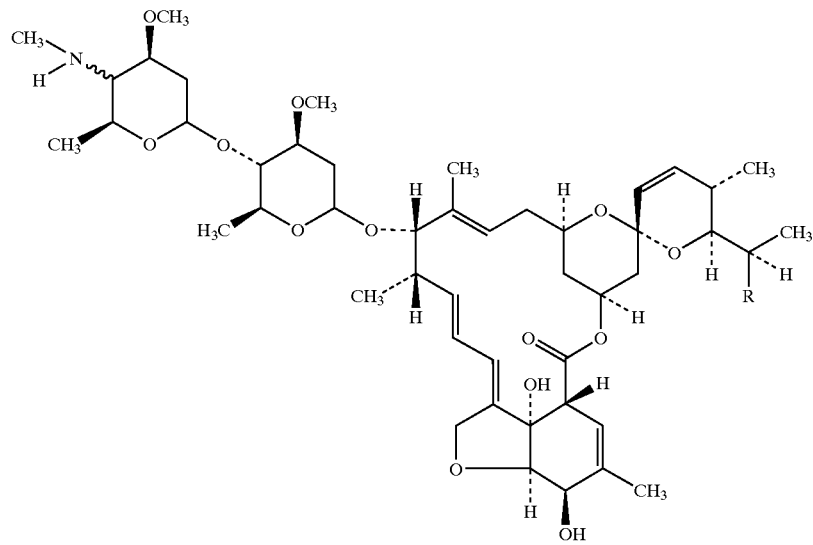

where R is —CH$_2$CH$_3$ or —CH$_3$, or a salt of this compound. These compounds are described in U.S. Pat. Nos. 4,874,749 or 5,288,710.

The alkyl radicals of the definition of the compounds (A) of the formula (I) generally comprise from 1 to 6 carbon atoms. The ring formed by the divalent alkylene radical representing R$_5$ and R$_6$ and the nitrogen atom to which R$_5$ and R$_6$ are attached is generally a 5-, 6- or 7-membered ring.

A preferred class of compounds (A) of formula (I) comprises the compounds such that R$_1$ is CN, R$_3$ is haloalkyl, R$_4$ is NH$_2$, R$_{11}$ and R$_{12}$ are, independently of one another, a halogen atom and R$_{13}$ is haloalkyl. Preferably still, X is C—R$_{12}$. A compound of formula (I) which is very particularly preferred in the invention is 1-[2,6-Cl$_2$-4-CF$_3$phenyl]-3-CN-4-[ SO—CF$_3$]-5-NH$_2$pyrazole or fipronil.

More generally, compounds (A) are pyrazoles such as phenylpyrazoles and N-arylpyrazoles, and reference is made to, for example, U.S. Pat. No. 5,567,429, U.S. Pat. No. 5,122,530, EP 295,117, and EP 846,686 A1 (or Banks GB 9,625,045, filed Nov. 30, 1996 also believed to be equivalent to U.S. Ser. No. 309,229, filed Nov. 17, 1997).

Compounds of formula (I) can be prepared according to one or other of the processes described in Patent Applications WO 87/3781, 93/6089 and 94/21606 or European Patent Application 295,117 or any other process coming within the competence of a person skilled in the art who is an expert in chemical synthesis. For the chemical preparation of the products of the invention, a person skilled in the art is regarded as having at his disposal, inter alia, the entire contents of "Chemical Abstracts" and of the documents which are cited therein.

Administration of the inventive formulation may be intermittent in time and may be administered daily, weekly, biweekly, monthly, bimonthly, quarterly, or even for longer durations of time. The time period between treatments depends upon factors such as the parasite(s) being treated, the degree of infestation, the type of mammal or bird and the environment where it resides. It is well within the skill level of the practitioner to determine a specific administration period for a particular situation. This invention contemplates a method for permanently combating a parasite in an environment in which the animal is subjected to strong parasitic pressure where the administration is at a frequency far below a daily administration in this case. For example, it is preferable for the treatment according to the invention to be carried out monthly on dogs and on cats.

Spot-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host. The compounds may be administered continuously, particularly for prophylaxis, by known methods. Generally, a dose of from about 0.001 to about 10 mg per kg of body weight given as a single dose or in divided doses for a period of from 1 to 5 days will be satisfactory but, of course, there can be instance where higher or lower dosage ranges are indicated and such are within the scope of this invention. It is well within the routine skill of the practitioner to determine a particular dosing regimen for a specific host and parasite.

Preferably, a single formulation containing the compounds (A) and (B) in a substantially liquid carrier and in a form which makes possible a single application, or an application repeated a small number of times, will be administered to the animal over a highly localized region of the animal, preferably between the two shoulders. Remarkably, it has been discovered that such a formulation is highly effective against both the targeted ectoparasites and the targeted endoparasites.

The treatment is preferably carried out so as to administer to the host, on a single occasion, a dose containing between about 0.001 and about 100 mg/kg of derivative (A) and containing between about 0.1 and about 2000 μg/kg, more preferably 1000 μg/kg of compound of type (B), in particular in the case of a direct topical administration.

The amount of compound (A) for birds and animals which are small in size is preferably greater than about 0.01 mg and in a particularly preferred way between about 1 and about 50 mg/kg of weight of animal.

It also may be preferable to use controlled-release formulations. However, due to the persistence of the activity of fipronil and of compounds (B), it may be preferable for reasons of simplicity to use conventional vehicles.

This invention also provides for a method for cleaning the coats and the skin of animals by removal of the parasites which are present and of their waste and excreta. The animals treated thus exhibit a coat which is more pleasing to the eye and more pleasant to the touch.

While not wishing to be bound by theory, it is believed that the invention spot-on formulation work by the dose dissolving in the natural oils of the host's skin, fur or feathers. From there, the therapeutic agent(s) distribute around the host's body through the sebaceous glands of the skin. The therapeutic agent also remains in the sebaceous glands. Thus, the glands provide a natural reservoir for the therapeutic agent which allows for the agent to be drained back out to the follicles to reapply itself to the skin and hair. This, in turn, provides for longer time periods between application as well as not having to re-administer the dose after the host becomes wet because of rain, bathes, etc. Moreover, the inventive formulation have the further advantage in self-grooming animals of not being directly deposited of the skin or fir where the animals could orally ingest the therapeutic agent, thereby becoming sick or possibly interacting with other therapeutic agent being orally administered.

The invention also relates to such a method with a therapeutic aim intended for the treatment and prevention of parasitoses having pathogenic consequences.

In another preferred embodiment this provides for a composition for combating fleas in small mammals, in particular dogs and cats, characterized in that it contains at least one compound (A) of formula (I) as defined above and at least one endectocidal compound (B), in amounts and proportions having a parasitical effectiveness for fleas and worms, in a vehicle acceptable for the animal.

The preferred class of compounds of formula (I) is that which has been defined above.

A compound of formula (I) which is very particularly preferred in the invention is 1-[2,6-Cl$_2$-4-CF$_3$ phenyl]-3-CN-4-[SO—CF$_3$]-5-NH$_2$ pyrazole.

Among the compounds of type (B), for small animals, a compound selected from the group formed by ivermectin, selamectin, emamectin and milbemectin is especially preferred.

The effective amount in a dose is, for the compound (A), preferably between about 0.001, preferentially about 0.1, and about 100 mg and in a particularly preferred way from about 1 to about 50 mg/kg of weight of animal, the higher amounts being provided for very prolonged release in or on the body of the animal.

The effective amount of compounds (B) in a dose is preferably between about 0.1 $\mu$g, preferentially about 1 $\mu$g, and about 10 mg and in a particularly preferred way from about 5 to about 200 $\mu$g/kg of weight of animal. Especially preferred is a dose between about 0.1 to about 10 mg/kg of weight of animal, with about 0.5 to 6 mg/kg being most especially preferred.

The proportions, by weight, of compound (A) and of compound (B) are preferably between about 5/1 and about 10,000/1.

The formulations of the present invention provide for the topical administration of a concentrated solution, suspension, microemulsion or emulsion for intermittent application to a spot on the animal, generally between the two shoulders (solution of spot-on type). It has been discovered that the inventive formulations are especially active against parasites when the formulations are applied to mammals and birds, especially poultry, dogs, cats, sheep, pigs, cattle and horses. These formulations comprise a composition of an effective amount of compound A and/or compound B dissolved in a pharmaceutical or veterinary acceptable carrier vehicle where a crystallization inhibitor is optionally present. Compound of (A) can advantageously be present in this formulation in a proportion of about 1 to about 20%, preferably of about 5 to about 15% (percentages as weight by volume=W/V). The liquid carrier vehicle comprises a pharmaceutically or veterinary acceptable organic solvent and optionally an organic cosolvent.

An especially preferred embodiment is spot-on formulation comprising a compound of formula (I) and emamectin or a salt thereof, with spot-on formulations comprising fipronil and emamectin being most especially preferred. It was discovered that a spot-on combination comprising a compound of formula (I) and emamectin or a salt thereof exhibited significantly greater efficacy against flea and ticks then a compound of formula (I) overtime.

Also contemplated are the pharmaceutically or veterinary acceptable acid or base salts, where applicable, of the active compounds provided for herein. The term "acid" contemplates all pharmaceutically or veterinary acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically or veterinary acceptable aliphatic, alicyclic and aromatic carboxylic acids, dicarboxylic acids tricarboxylic acids and fatty acids. Preferred acids are straight chain or branched, saturated or unsaturated $C_1$–$C_{20}$ aliphatic carboxylic acids, which are optionally substituted by halogen or by hydroxyl groups, or $C_6$-$Cl_2$ aromatic carboxylic acids. Examples of such acids are carbonic acid, formic acid, fumaric acid, acetic acid, propionic acid, isopropionic acid, valeric acid, $\alpha$-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically or veterinary acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all pharmaceutically or veterinary acceptable inorganic or organic bases. Such bases include, for example, the alkali metal and alkaline earth metal salts, such as the lithium, sodium, potassium, magnesium or calcium salts. Organic bases include the common hydrocarbyl and heterocyclic amine salts, which include, for example, the morpholine and piperidine salts.

Preferred salts for emamectin include the acid mineral salts, such as the hydrochloride, nitrate, sulfate, phosphate salts, and the organic acids such as the tartarate and malate salts. Especially preferred salts are salts of the formula:

X.

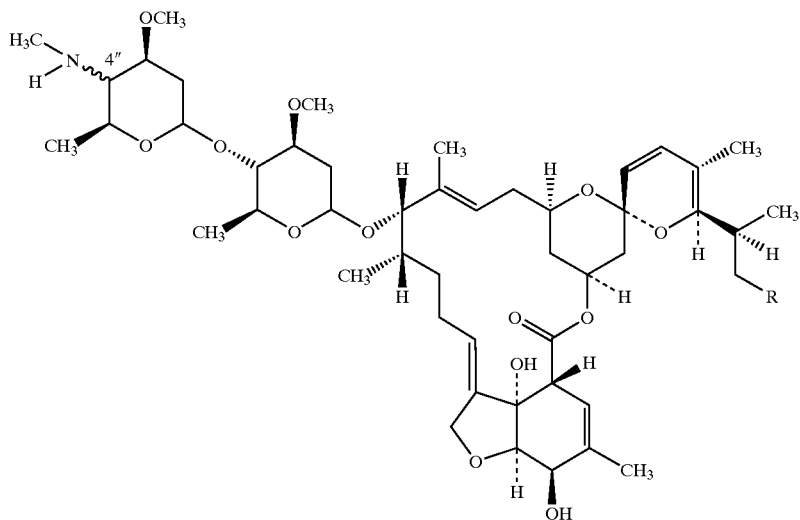

wherein
R is hydrogen or methyl; and
X is:
a) benzoic acid,
b) benzoic acid substituted with one, two, or three substituents selected from the group consisting of:
  i) halogen (Cl, Br, F, I),
  ii) hydroxyl,
  iii) carboxyl,
  iv) ($C_1$–$C_6$)-alkyl, and
  v) ($C_1$–$C_6$)-alkoxyl,
c) benzenesulfonic acid,
d) citric acid,
e) phosphoric acid,
f) tartaric acid, or
g) maleic acid.

The organic solvent for the liquid carrier vehicle will preferably have a dielectric constant of between about 10 and about 35, preferably between about 20 and about 30, the content of this solvent in the overall composition preferably representing the remainder to 100% of the composition. It is well within the skill level of the practitioner to select a suitable solvent on the basis of these parameters.

The organic cosolvent for the liquid carrier vehicle will preferably have a boiling point of less than about 100° C., preferably of less than about 80° C., and will have a dielectric constant of between about 10 and about 40, preferably between about 20 and about 30; this cosolvent can advantageously be present in the composition according to a weight/weight (W/W) ratio with respect to the solvent of between about 1/15 and about 1/2; the cosolvent is volatile in order to act in particular as drying promoter and is miscible with water and/or with the solvent. Again, it is well within the skill level of the practitioner to select a suitable solvent on the basis of these parameters.

The organic solvent for the liquid carrier includes the commonly acceptable organic solvents known in the formulation art. These solvents may be found, for example, in Remington Pharmaceutical Science, 16$^{th}$ Edition (1986). These solvents include, for example, acetone, ethyl acetate, methanol, ethanol, isopropanol, dimethylformamide, dichloromethane or diethylene glycol monoethyl ether (Transcutol). These solvents can be supplemented by various excipients according to the nature of the desired phases, such as $C_8$–$C_{10}$ caprylic/capric triglyceride (Estasan or Miglyol 812), oleic acid or propylene glycol.

The liquid carrier may also comprise a microemulsion. Microemulsions are also well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

The oily phase can in particular be formed from mineral or vegetable oils, from unsaturated polyglycosylated glycerides or from triglycerides, or alternatively from mixtures of such compounds. The oily phase preferably comprises triglycerides and more preferably medium-chain triglycerides, for example $C_8$–$C_{10}$ caprylic/capric triglyceride. The oily phase will represent, in particular, from about 2 to about 15%, more particularly from about 7 to about 10%, preferably from about 8 to about 9%, V/V of the microemulsion.

The aqueous phase includes, for example water or glycol derivatives, such as propylene glycol, glycol ethers, polyethylene glycols or glycerol. Propylene glycol, diethylene glycol monoethyl ether and dipropylene glycol monoethyl ether are especially preferred. Generally, the aqueous phase will represent a proportion from about 1 to about 4% V/V in the microemulsion.

Surfactants for the microemulsion include diethylene glycol monoethyl ether, dipropyelene glycol monomethyl ether, polyglycolysed $C_8$–$C_{10}$ glycerides or polyglyceryl-6 dioleate. In addition to these surfactants, the cosurfactants include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation.

The cosurfactant to surfactant ratio will preferably be from about 1/7 to about 1/2. There will preferably be from about 25 to about 75% V/V of surfactant and from about 10 to about 55% V/V of cosurfactant in the microemulsion.

Likewise, the co-solvents are also well known to a practitioner in the formulation art. Preferred co-solvents are those which is a promoter of drying and include, for example, absolute ethanol, isopropanol (2-propanol) or methanol.

The crystallization inhibitor can in particular be present in a proportion of about 1 to about 20% (W/V), preferably of about 5 to about 15%. The inhibitor preferably corresponds to the test in which 0.3 ml of a solution comprising 10% (W/V) of the compound of formula (I) in the liquid carrier and 10% of the inhibitor are deposited on a glass slide at 20° C. and allowed to stand for 24 hours. The slide is then observed with the naked eye. Acceptable inhibitors are those whose addition provides for few or no crystals, and in particular less than 10 crystals, preferably 0 crystals.

Although this is not preferred, the formulation can optionally comprise water, in particular in a proportion of 0 to about 30% (volume by volume V/V), in particular of 0 to about 5%.

The formulation can also comprise an antioxidizing agent intended to inhibit oxidation in air, this agent being in particular present in a proportion of about 0.005 to about 1% (W/V), preferably of about 0.01 to about 0.05%.

Crystallization inhibitors which can be used in the invention include:
  polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others,
  anionic surfactants, such as alkaline stearates, in particular sodium, potassium or ammonium stearate; calcium stearate or triethanolamine stearate; sodium abietate; alkyl sulphates, in particular sodium lauryl sulphate and sodium cetyl sulphate; sodium dodecylbenzenesulphonate or sodium dioctyl sulphosuccinate; or fatty acids, in particular those derived from coconut oil,
  cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulphate and sulphonate anions; cetyltrimethylammonium bromide is one of the cationic surfactants which can be used,
  amine salts of formula $N^+R'R''R'''$, in which the R radicals are identical or different optionally hydroxylated hydrocarbon radicals; octadecylamine hydrochloride is one of the cationic surfactants which can be used,
  non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide,
  amphoteric surfactants, such as substituted lauryl compounds of betaine,
  or preferably a mixture of at least two of the compounds listed above.

In a particularly preferred embodiment, a crystallization inhibitor pair will be used. Such pairs include, for example, the combination of a film-forming agent of polymeric type and of a surface-active agent. These agents will be selected in particular from the compounds mentioned above as crystallization inhibitor.

Particularly preferred film-forming agents of polymeric type include:
  the various grades of polyvinylpyrrolidone,
  polyvinyl alcohols, and
  copolymers of vinyl acetate and of vinylpyrrolidone.

Especially preferred surface-active agents, include those made of non-ionic surfactants, preferably polyoxyethylenated esters of sorbitan and in particular the various grades of polysorbate, for example Polysorbate 80.

The film-forming agent and the surface-active agent can in particular be incorporated in similar or identical amounts within the limit of the total amounts of crystallization inhibitor mentioned elsewhere.

The pair thus constituted secures, in a noteworthy way, the objectives of absence of crystallization on the coat and of maintenance of the cosmetic appearance of the fur, that is to say without a tendency towards sticking or towards a sticky appearance, despite the high concentration of active material.

Particularly preferred antioxidizing agents are those conventional in the art and include, for example, butylated hydroxyanisole, butylated hydroxytoluene, ascorbic acid, sodium metabisulphite, propyl gallate, sodium thiosulphate or a mixture of not more than two of them.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume applied can be of the order of about 0.3 to about 1 ml, preferably of the order of about 0.5 ml, for cats and of the order of about 0.3 to about 3 ml for dogs, depending on the weight of the animal.

An especially preferred compound (A) is a derivative of formula (II):

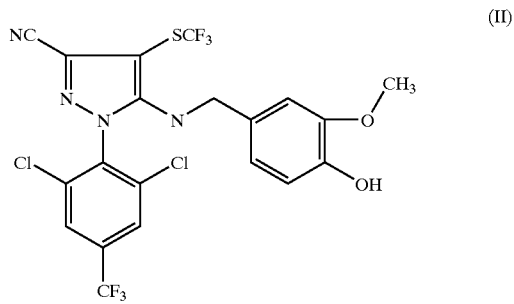

(II)

The formulations according to the invention are extremely effective for long durations of time in the treatment of parasites such as fleas of mammals and, in particular, of small mammals such as dogs and cats. The inventive formulations exhibit a degree of effectiveness against other parasitic insects and in particular ticks, mites, mosquitoes and flies. Moreover, the inventive formulations are also extremely effective for a long duration in the treatment of endoparasites, such as the dirofilariasis parasite and/or roundworms. The inventive formulations further exhibit synergy when treating infestations cause by ectoparasites and endoparasites. A particularly preferred synergistic formulation for the treatment of filariae and roundworms comprises fipronil and milbemectin, fipronil and selamectin or fipronil and emamectin.

This invention also provides for the use of at least one compound of formula (I) and of at least one compound of type (B), as defined above, in the preparation of a composition as defined above.

Other advantages and characteristics of the invention will become apparent on reading the following description, given by way of non-limiting examples.

EXAMPLES

Example 1

Preparation of a Concentrated Solution for Intermittent Application (Spot-On)

A concentrated solution for cutaneous application is prepared which contains, as weight by volume of solution, 10% of fipronil and 0.25% of ivermectin. The administration volume is 1 ml per 10 kg of animal weight. The composition is as follows, as weight/volume:

| | |
|---|---|
| fipronil: | 10% |
| ivermectin | 0.25% |
| Polyvinylpyrrolidone (Kollidon 17 PF): | 5% |
| Polysorbate 80 (Tween 80): | 5% |
| ethanol: | 10% |
| Transcutol: | q.s. for 100% |

Example 2

Preparation of a Concentrated Microemulsion for Intermittent Application (Spot-On)

The ingredients used are as follows:

oily phase: $C_8$–$C_{10}$ caprylic/capric triglyceride (Estasan)

aqueous phase: propylene glycol surfactant: diethylene glycol monoethyl ether (Transcutol)

cosurfactant: ethanol or 2-propanol crystallization inhibitor pair: Polysorbate 80 (Tween 80) and polyvinylpyrrolidone (Kollidon 17 PF).

| A composition example contains: | |
|---|---|
| fipronil: | 10 g |
| ivermectin: | 0.5 g |
| Estasan: | 8.5 ml |
| Transcutol: | 60 ml |
| ethanol: | 15 ml |
| Kollidon 17 PF: | 5 g |
| Tween 80: | 5 g |
| propylene glycol: | q.s. for 100 ml. |

In the formulation described, the Transcutol acts as the surfactant (SA) and the ethanol or 2-propanol acts as cosurfactant (Co-SA). They make it possible to obtain, from a mixture of medium-chain triglycerides (Estasan) which is immiscible with propylene glycol, an isotropic transparent microemulsion. The crystallization inhibitor pair will be added once the microemulsion has been formed.

Example 3

Five dogs weighing 12 kg, deprived of food, receive the application of 1 ml of composition according to Example 2 or 3, i.e. 100 mg of fipronil and 2.5 mg of ivermectin, by localized cutaneous application between the two shoulders. The measurements carried out on the plasma of the animals show the production of an ivermectin peak of 1000 to 1500 to 2000 pg/ml.

A monthly or even bimonthly treatment of dogs makes possible complete control of fleas, ticks and dirofilariasis parasites.

Example 4

Plasma Kinetics of Ivermectin after Oral Administration of Cardomec® at the Dose of 6 $\mu$g.kg$^{-1}$ to Dogs This example was conducted in order to demonstrate the pharmacokinetics of ivermectin in the dog after oral administration of Cardomec® at a dose of 6 $\mu$g.kg$^{-1}$ of ivermectin which is known to be 100% effective on heartworms and to have a route of reference for further development.

Five male Beagle dogs received a dose of approximately 6 $\mu$g.kg$^{-1}$ of ivermectin, i.e., one 68 $\mu$g Cardomec® tablet per dog. The animals were fasted prior to administration and up to 6 hours after treatment to prevent a possible interaction with food.

Blood samples were collected at intervals up to 28 days post-dosing. The determination of ivermectin in dog plasma was carried out by HPLC using fluorescence detection after derivatization. The limit of quantification was 100 pg.ml$^{-1}$.

Ivermectin could be quantified in dog plasma up to day 1 or 7, depending on the dog (Table 1). The profiles were very variable, presenting a first order absorption with one or two peaks and a biexponential depletion.

The pharmacokinetic parameters were very variable (Tables 2 and 3). $C_{max}$ ranged between 422 and 2964 pg.ml$^{-1}$, $t_{max}$ between 3 and 12 h, AUC between 9164 and 90938 pg.h.ml$^{-1}$. The ratio between the highest and smallest $C_{max}$ was 7, the differences even more striking for $AUC_{(0-t)}$ and AUC with ratios of 17 and 10 respectively. Compared with the other parameters, the terminal half-lives (t½) were relatively similar between animals (CV<40%), ranging between 26.0 and 64.5 h, i.e. 1.08 day and 2.69 days. The mean value of the terminal half-life was 40.1 h (1.67 d).

The mean pharmacokinetic parameters determined from the present study are in good agreement with the literature: 3 h for $t_{max}$ compared with the literature data of 2–4 hours, t½=1.67 d against 1.6 to 1.8 d in the literature. $C_{max}$ and AUC only were low with values of 1362 pg.ml$^{-1}$ and 44604 pg.h.ml$^{-1}$ versus mean literature values of more than 2000 pg.ml$^{-1}$ and 107318 pg.h.ml$^{-1}$, respectively. This experiment was conducted on fasted animals. Some prior articles mentioned a possible interaction of ivermectin with food, without the food state of the dogs being specified. It is possible that they were unfasted and that food interacts positively with ivermectin absorption, i.e., increases the rate and extent of absorption of ivermectin and therefore leads to higher $C_{max}$ and AUC than in the present experiment.

Two conclusions can be drawn from this study: the inter-animal variability is an important feature and the terminal half-lives are relatively constant (around 2 days).

Example 5

Efficacy against Ticks of a Topical Composition According to the Present Invention against Ticks The following composition according to the present invention was prepared:

Inventive Composition

| Component | % Component (w/v) |
|---|---|
| Fipronil | 10% |
| Emamectin | 0.5% |
| Ethanol | 10% |
| Polyvidene | 5% |
| Tween 80 | 5% |
| BHT | 0.01% |
| BHA | 0.02% |
| Diethylene Glycol Monomethyl ether | qs 100% |

The following comparison topical composition was prepared:

Comparative-Example 1

PLACEBO

| Component | % Component (w/v) |
|---|---|
| Ethanol | 10% |
| Polyvidone | 5% |
| Tween 80 | 5% |
| BHT | 0.01% |
| BHA | 0.02% |
| Diethylene Glycol Monomethyl ether | qs 100% |

Comparative-Example 2

FRONTLINE

| Component | % Component (w/v) |
|---|---|
| Finopril | 10% |
| Ethanol | 10% |
| Polyvidone | 5% |
| Tween 80 | 5% |
| BHT | 0.01% |
| BHA | 0.02% |
| Diethylene Glycol Monomethyl ether | qs 100% |

Comparative-Example 3

EMAMECTIN

| Component | % Component (w/v) |
|---|---|
| Emamectin | 0.5% |
| Ethanol | 10% |
| Polyvidone | 5% |
| Tween80 | 5% |
| BHT | 0.01% |
| BHA | 0.02% |
| Diethylene Glycol Monomethyl ether | qs 100% |

The inventive composition and the comparative composition were tested for their effectiveness on the flea and tick infestations on dogs. Beagles were infested with approximately 50 *Rhipicephalus sanguineus* (ticks) on days 14, 20, 27, 34, 41, 48 and 62 and with approximately 100 *Ctenocephalides felis* on days 15, 28, 42, and 70. The fleas were counted and removed 24 hour after each infestation and the ticks were counted and removed from all dogs after 48 hours of infestation. There were four dogs in each group. A topical formulation dosage rates 1.0 ml/10 kg of body weight of the topical formulation was applied on the midline of the neck, between the base of the skull and the shoulder blade. Table I reports the average percent efficiency against flea and tick counts for each of the biological example compared to the placebo.

TABLE 1

| Composition | Fleas Day 16 | Ticks Day 16 | Ticks Day 22 | Fleas Day 29 | Ticks Day 36 | Ticks Day 36 | Fleas Day 43 | Ticks Day 43 | Ticks Day 50 | Ticks Day 64 | Fleas Day 71 |
|---|---|---|---|---|---|---|---|---|---|---|---|
| Comparative 2 | 100.0 | 100.0 | 100.0 | 100.0 | 93.6 | 99.2 | 96.4 | 85.8 | 74.5 | 54.9 | 32.9 |
| Comparative 3 | 31.2 | 29.4 | 35.0 | ND | ND | ND | ND | ND | 38.8 | 36.9 | 0.3 |
| Inventive Composition | 100.0 | 99.4 | 100.0 | 100.0 | 98.2 | 100.0 | 98.9 | 95.3 | 88.9 | 64.8 | 72.2 |

The data presented in Table I demonstrate that the inventive composition exhibits a far greater efficacy against fleas and ticks than either fipronil or emamectin alone. FIG. 1 depicts the comparison of the inventive composition against a composition comprising fipronil against ticks. FIG. 2 depicts the comparison of the inventive composition against a composition comprising fipronil against fleas.

The above description of the invention is intended to be illustrative and not limiting. Various changes or modifications in the embodiments described herein may occur to those skilled in the art. These can be made without departing from the scope and spirit of the invention.

What is claimed:

1. A spot-on formulation for the treatment or prophylaxis of parasite infestation in mammals or birds which comprises (1) a composition comprising (A) an effective amount of at least one compound of the formula

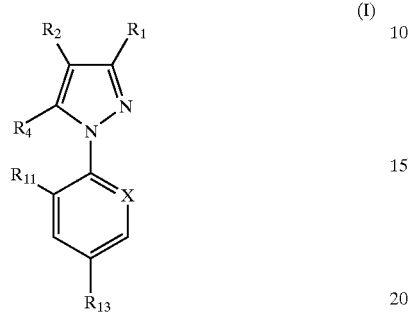

in which:

$R_1$ is a halogen, CN or methyl;

$R_2$ is $-S(O)_nR_3$, 4,5-dicyanoimidazol-2-yl, haloalkyl;

$R_3$ is alkyl or haloalkyl;

$R_4$ represents hydrogen halogen atom, $NR_5R_6$, $-S(O)_mR_7$, $-C(O)R_7-C(O)OR_7$, alkyl, haloalkyl, $OR_8$ or $-N=C(R_9)(R_{10})$;

$R_5$ and $R_6$ independently represent hydrogen, alkyl, haloalkyl, $-C(O)$alkyl, $-S(O)_rCF_3$ or alkoxycarbonyl or $R_5$ and $R_6$ together form a divalent alkylene radical which is optionally interrupted by one or two divalent heteroatoms;

$R_7$ represents alkyl or haloalkyl;

$R_8$ represents hydrogen alkyl or haloalkyl;

$R_9$ represents hydrogen or alkyl;

$R_{10}$ represents an optionally substituted aryl or an optionally substituted heteroaryl group;

$R_{11}$ and $R_{12}$ represent, independently of one another, hydrogen, halogen CN or $NO_2$;

$R_{13}$ represents halogen haloalkyl, haloalkoxy, $S(O)_qCF_3$ or $SF_5$ group;

m, n, q and r represent, independently of one another, an integer equal to 0, 1 or 2;

X represents a trivalent nitrogen atom or a $C-R_{12}$ radical, the three other valencies of the carbon atom forming part of the aromatic ring;

with the proviso that, when $R_1$ is methyl, then either $R_3$ is haloalkyl, $R_4$ is $NH_2$, $R_{11}$ is Cl, $R_{13}$ is $CF_3$ and X is N or else $R_2$ is 4,5-dicyanoimidazol-2-yl, $R_4$ is Cl, $R_{11}$ is Cl, $R_{13}$ is $CF_3$ and X is C—Cl; and (B) an effective amount of emamectin or a salt thereof;

(2) a pharmaceutically or veterinary acceptable liquid carrier vehicle; and (3) optionally, a crystallization inhibitor.

2. The spot-on formulation according to claim 1, which comprises:

(1) a composition comprising (A) an effective amount of a compound of formula (I) wherein $R_1$ is a halogen, CN or methyl;

$R_2$ is $-S(O)_nR_3$, 4,5-dicyanoimidazol-2-yl or haloalkyl;

$R_3$ is $C_1-C_6$-alkyl or $C_1-C_6$-haloalkyl;

$R_4$ represents hydrogen, halogen $-NR_5R_6$, $-S(O)_mR_7$, $-C(O)R_7-C(O)OR_7$, $C_1-C_6$-alkyl, $C_1-C_6$-haloalkyl, $OR_8$ or $-N=C(R_9)(R_{10})$;

$R_5$ and $R_6$ independently represent hydrogen $C_1-C_6$-alkyl, $C_1-C_6$-haloalkyl, $-C(O)C_1-C_6$-alkyl, $-S(O)_rCF_3$, $C_1-C_6$-acyl or $C_1-C_6$-alkoxycarbonyl radical; or $R_5$ and $R_6$ may together form a divalent alkylene radical which may be interrupted by one or two divalent hetero atoms selected from the group consisting of oxygen or sulphur;

$R_7$ represents $C_1-C_6$-alkyl or $C_1-C_6$-haloalkyl;

$R_8$ represents hydrogen, $C_1-C_6$-alkyl or $C_1-C_6$-haloalkyl;

$R_9$ represents hydrogen $C_1-C_6$-alkyl radical;

$R_{10}$ represents an optionally substituted phenyl or optionally substituted heteroaryl group wherein the substituents are selected from the group consisting of halogen, OH, $-O-(C_1-C_6)$-alkyl, $-S-(C_1-C_6)$-alkyl, cyano or $C_1-C_6$-alkyl;

$R_{11}$ and $R_{12}$, independently of one another represent hydrogen, halogen, CN or $NO_2$;

$R_{13}$ represents a halogen, $C_1-C_6$-haloalkyl, $C_1-C_6$-haloalkoxy, $S(O)_qCl_3$ or $SF_5$ group, and/or (B) an effective amount of emamectin or a salt thereof;

(2) the liquid carrier vehicle comprises a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylaceamide, dipropylene glycol monomethyl ether, liquid polyoxyethylene glycols, propylene glycol, 2-pyrrolidone, diethylene glycol monoethyl ether, diethylene glycol monomethyl ether, ethylene glycol, diethyl phthalate, and a mixture of at least two of these solvents and the cosolvent is selected from the group consisting of absolute ethanol, ethanol isopropanol or methanol;

(3) a crystallization inhibitor selected from the group consisting of an anionic surfactant, a cationic surfactant, a non-ionic surfactant, an amine salt, an amphoteric surfactant, polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, and acrylic derivatives, or a mixture of these crystallization inhibitors.

3. The spot-on formulation according to claim 2, wherein the crystallization inhibitor is present in an amount from about 1 to about 20% W/V.

4. The spot-on formulation according to claim 1 which comprises a crystallization inhibitor.

5. The spot-on formulation according to claim 1, wherein the combination comprises (1) 1-[2,6-$Cl_2$-4-$CF_3$ phenyl]-3-CN-4-[SO—$CF_3$]-5-$NH_2$ pyrazole; and (2) emamectin.

6. The spot-on formulation according to claim 1, wherein the liquid carrier vehicle comprises a microemulsion.

7. The spot-on formulation according to claim 1, wherein the liquid carrier vehicle further comprises a diluent.

8. The spot-on formulation according to claim 1, wherein the combination comprises about 0.001 to about 100 mg/kg of weight of mammal or bird of a compound of formula (I)

and between about 0.1 mg to about 10 mg/kg of weight of mammal or bird of emamectin or a salt thereof.

9. The spot-on formulation according to claim 1, wherein the combination comprises about 1 to about 50 mg/kg of weight of mammal or bird of a compound of formula (I) and between about 0.1 µg to about 1 mg/kg per weight of mammal or bird of emamectin or a salt thereof.

10. The spot-on formulation according to claim 1, wherein the combination comprises between about 5 and about 500 µg/kg per weight of mammal or bird of emamectin or a salt thereof.

11. The spot-on formulation according to claim 5 which comprises about 0.5 mg/kg of emamectin per weight of mammal or bird.

12. The spot-on formulation according to claim 1, wherein the combination comprises the ratio, by weight, of a compound of formula (I) to macrocyclic lactone is about 5/1 to about 10,000/1.

13. The spot-on formulation according to claim 1, which further comprises an antioxidant.

14. The spot-on formulation according to claim 13, wherein about 0.005 to about 1% (W/V) of antioxidant is present and the antioxidant is selected from the group consisting of butylated hydroxyanisole, butylated hydroxytoluene, ascorbic acid, sodium metabisulphite, propyl gallate, and sodium thiosulphate.

15. The spot-on formulation according to claim 1, wherein water is present in a proportion of from 0 to about 30%. V/V.

16. The spot-on formulation according to claim 13, wherein the compound of formula (I) is fipronil, the liquid carrier vehicle is diethylene glycol monomethyl ether, the crystallization inhibitor is povidone and polysorbate 80 and the antioxidants are butylated hydroxyanisole and butylated hydroxytoluene.

17. A spot-on formulation for combating parasites in an animal which comprises fipronil, emamectin or a salt thereof, a vehicle for a localized cutaneous application to an animal with absorption and a resultant plasma concentration of parasiticides, wherein the vehicle contains dipropylene glycol monomethyl ether, or diethylene glycol monomethyl ether and ethanol, the crystallization inhibitor is polyvidone and polysorbate 80 and, optionally, at least one antioxidant.

18. The spot-on formulation according to claim 2, wherein
the anionic surfactant is alkaline stearates, sodium abietate; alkyl sulphates; sodium dodecylbenzenesulphonate, sodium dioctylsulphosuccinate; and fatty acids;
the cationic surfactant is water-soluble quaternary ammonium salts of formula $N^+R'R''R'''R''''Y^-$ in which the radicals R independently are hydrocarbon radicals, optionally hydroxylated, and $Y^-$ is an anion of a strong acid;
the amine salt is an amine salt of $N^+R'R''R'''$ in which the radicals R independently are optionally hydroxylated hydrocarbon radicals;
the non-ionic surfactant is optionally polyoxyethylenated sorbitan esters, polyoxyethylenated alkyl ethers; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide; and
the amphoteric surfactant is lauryl-substituted betaine compounds.

19. The spot-on formulation according to claim 18, where the crystallization inhibitor is a crystallization inhibitor system comprising a polymeric film-forming agent and a surfactant.

20. The spot-on formulation according to claim 19, wherein the polymeric film-forming agent is polyvinylpyrrolidone, polyvinyl alcohols, or a copolymer of vinyl acetate and polyvinylpyrrolidone and the surfactant is a non-ionic surfactant.

21. The spot-on formulation according to claim 19, wherein the crystallization inhibitor system is a mixture of polyvinylpyrrolidone and polyoxethylene (20) sorbitan mono-oleate.

22. A method of treating parasite infestations or for the prophylaxis of parasite infestation in mammals, fish or birds which comprises applying to said mammals, fish or birds an effective amount of a spot-on composition according to claim 1.

23. The method according to claim 22, wherein the parasite is an ectoparasite.

24. The method according to claim 22, wherein the parasite is an endoparasite.

25. The method according to claim 22, wherein the mammal is a cat, dog, horse, cattle or sheep.

26. The method according to claim 25, wherein the parasite is a flea or tick.

27. The method according to claim 22, wherein the mammal is a human.

28. The method according to claim 22, wherein the mammals are cattle and the parasite is *Boophilus microplus*.

29. The method according to claim 22, wherein the mammals are sheep and the parasite is lice and blowfly.

30. The method according to claim 22, wherein the ectoparasites are mites, mosquitoes, flies or a combination of the foregoing.

31. A method of treating parasite infestations or for the prophylaxis of parasite infestations in mammals or birds which comprises applying to said mammals or birds an effective amount of a spot-on formulation according to claim 5.

32. The method of claim 22, wherein the administration is bimonthly.

33. The method of claim 22, wherein the administration is quarterly.

34. The method of claim 22, wherein the administration is monthly.

35. The method of claim 31, wherein the administration is bimonthly.

36. The method of claim 31, wherein the administration is quarterly.

37. The method of claim 31, wherein the administration is monthly.

38. The spot-on formulation as claimed in claim 17, wherein an antioxidant is present and it is a mixture of BHT and BHA.

39. A method for combating parasites in a mammal comprising topically administering to a mammal a parasiticidally effective amount of a spot-on formulation according to claim 17.

40. The method according to claim 39, wherein the mammal is a cat or dog and the parasite is a flea or tick.

41. A method for obtaining a detectable plasma concentration of parasiticides in a mammal comprising topically applying to a localized area on said mammal a parasiticidally effective amount of the spot-on formulation as claimed in claim 17.

42. A method for combating parasites of a cat or dog comprising localized cutaneous application to the cat or dog, between the shoulders, at a frequency not greater than monthly, of a spot-on composition, which comprises, in a veterinarily acceptable vehicle, an amount parasitically effective of at least one compound (A), and an amount parasitically effective of at least one compound (B), wherein:

compound (A) is an ectoparasiticide of the formula (I)

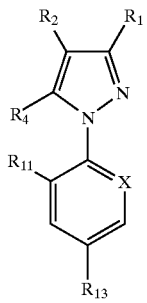

(I)

in which:
$R_1$ is CN;
$R_2$ is $S(O)_nR_3$;
$R_3$ is haloalkyl;
$R_4$ represents $NH_2$;
$R_{11}$ represents halogen atom;
$R_{13}$ represents haloalkyl;
n represents an integer equal to 0, 1 or 2;
X represents a radical C—$R_{12}$;
$R_{12}$ represents a halogen atom; and
compound (B) is an endectocidal parasiticide which is emamectin or a salt thereof and,
the vehicle is for a localized cutaneous application to the animal between the shoulders and contains an organic solvent, an organic cosolvent and/or a crystallization inhibitor wherein:
the crystallization inhibitor selected from the group consisting of polyvinylpyrrolidone, copolymers of vinyl acetate and vinylpyrrolidone, polyoxyethylenated sorbitan esters and mixtures thereof;
the organic solvent comprises acetone, ethyl acetate, methanol, ethanol, isopropanol, dimethylformamide, dichloromethane or diethyl glycol monoethyl ether; said solvent optionally supplemented by $C_8$–$C_{10}$ caprylic/capric triglyceride, oleic acid or propylene glycol; and
the organic cosolvent selected from the group consisting of ethanol, isopropanol, and methanol;
whereby there is a prolonged release of compound (A) in or on the body of the cat or dog and there is a measurable plasma level of compound (B) in the cat or dog.

43. The method of claim 42 wherein in the spot-on composition compound (A) is 1-[4-$CF_3$ 2,6-$Cl_2$ phenyl]3-cyano 4-[$CF_3$—SO] 5-$NH_2$ pyrazole.

44. The method of claim 43 wherein compound (A) is present in the spot-on composition in an amount of from 0.1 to 100 mg/kg of weight of animal and compound (B) is present in the spot-on composition in an amount of from 1 $\mu$g to 1 mg/kg of weight of animal.

45. The method of claim 42 wherein the crystallization inhibitor in the spot-on composition is a crystallization inhibitor pair.

46. The method according to claim 42 wherein the organic solvent in the spot-on composition is diethylene glycol monoethyl ether and the organic cosolvent in the spot-on composition is ethanol or isopropanol.

47. The method of claim 43 wherein there is a weight/weight ratio of the cosolvent/solvent in the spot-on composition and the weight/weight ratio of the cosolvent/solvent is between 1/15 and 1/2.

48. The method of claim 43 wherein the spot-on composition further comprises water in an amount of less than 30% (volume/volume).

49. The method of claim 43 wherein the spot-on composition does not contain water.

50. The method of claim 43 wherein the spot-on composition further comprises an antioxidant.

51. The method of claim 50 wherein the antioxidant in present in the spot-on composition in an amount of 0.005 to 1% weight/volume and is selected from the group consisting of butylated hydroxyanisole, butylated hydroxytoluene, ascorbic acid, sodium metabisulphite, propyl gallate, and sodium thiosulphate.

* * * * *